(12) United States Patent
Philippe et al.

(10) Patent No.: US 6,365,135 B1
(45) Date of Patent: Apr. 2, 2002

(54) USE OF AMINO PHENOL AMIDE DERIVATIVES AS DEPIGMENTATION AGENTS

(75) Inventors: Michel Philippe, Wissous; Remy Tuloup, Paris; Christine Duval, Vincennes, all of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/355,968

(22) PCT Filed: Nov. 27, 1998

(86) PCT No.: PCT/FR98/02562

§ 371 Date: Nov. 10, 1999

§ 102(e) Date: Nov. 10, 1999

(87) PCT Pub. No.: WO99/32077

PCT Pub. Date: Jul. 1, 1999

(30) Foreign Application Priority Data

Dec. 19, 1997 (FR) ............................................ 97 16171

(51) Int. Cl.[7] .................. A61K 7/135; A61K 7/04; A61K 7/06; A61K 6/00; A01N 25/34
(52) U.S. Cl. .................. 424/62; 424/61; 424/70.1; 424/401; 424/404
(58) Field of Search .................. 424/61, 70.1, 404, 424/62, 401

(56) References Cited

U.S. PATENT DOCUMENTS 5,104,414 A * 4/1992 Tamura et al. .................. 8/408

FOREIGN PATENT DOCUMENTS

| FR | 2 760 191 | | 9/1998 |
|---|---|---|---|
| JP | 7-61905 | | 3/1995 |
| JP | 7-233022 | * | 5/1995 |
| JP | 7-061905 | * | 7/1995 |
| JP | 7-233022 | | 9/1995 |
| WO | WO 98 24407 | | 6/1998 |

OTHER PUBLICATIONS

Stn, Serveur de Bases de Donnees, Fichier, XP002076207, Chemical Abstracts, vol. 122, AN–298716.
Tada et al, "Synthesis of karahanaenone derivatives and their inhibition properties toward tyrosinase and superoxide scavenging activity", *Biosci., Biotechnol., Biochem.*, vol. 60, No. 9, 1996, pp. 1421–1424.
Boekelheide et al, "Synthesis of y–1–glutaminyl–'3,5–h 4–hydroxybenzene and the study of reactions catalyzed by the tyrostinase of Agaricus Bisporus", *J. Biol. Chem.*, vol. 254, No. 23, Dec. 10, 1979, pp. 12185–12191.
Boekelheide et al, "Melanocytotoxicity and the machanism of y–L–glutaminyl–4–hyroxybenzene", *J. Invest. Dermatol.*, vol. 75, No. 4, 1980, pp. 322–327.

* cited by examiner

Primary Examiner—Thurman K. Page
Assistant Examiner—S. Tran
(74) Attorney, Agent, or Firm—Oblon, Spivak, McClelland, Maier & Neustadt, P.C.

(57) ABSTRACT

The invention relates to the use of aminophenol amide derivatives in a composition as an agent for depigmenting and/or bleaching human skin, body hairs and/or head hair. The invention also relates to a process for depigmenting and/or bleaching the skin, body hairs and/or head hair, which consists in applying a composition comprising aminophenol amide derivatives to human skin, body hairs and/or head hair.

9 Claims, No Drawings

USE OF AMINO PHENOL AMIDE DERIVATIVES AS DEPIGMENTATION AGENTS

This application is a 371 of PCT/FR98/02562 filed Nov. 27, 1998.

The present invention relates to the use of aminophenol amide derivatives as depigmenting or bleaching agents in a cosmetic and/or dermatological composition, and to a depigmenting and/or bleaching composition containing aminophenol amide derivatives.

The colour of human skin depends on various factors and, in particular, the seasons of the year, race and sex, and it is mainly determined by the nature and concentration of melanin produced by the melanocytes. Melanocytes are specialized cells which synthesize melanin by means of specific organelles, the melanosomes. In addition, at different periods in their life, certain individuals develop darker and/or more coloured blemishes on the skin and more especially on the hands, making the skin non-uniform. These blemishes are also due to a large concentration of melanin in the keratinocytes located at the skin surface.

In the same way, the colour of head hair and body hairs is due to melanin. When head hair or body hairs are dark, certain people wish them to be lighter. This is particularly advantageous for hairs which are less visible when they are light than when they are dark.

The mechanism for the formation of skin pigmentation, and pigmentation of head hair and body hairs, that is to say the formation of melanin, is particularly complex and schematically involves the following main steps:

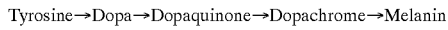

Tyrosine→Dopa→Dopaquinone→Dopachrome→Melanin

Tyrosinase (monophenol dihydroxyl phenylalanine: oxygen oxidoreductase EC 1.14.18.1) is the essential enzyme involved in this reaction sequence. It especially catalyses the reaction for the conversion of tyrosine into dopa (dihydroxyphenylalanine) by virtue of its hydroxylase activity and the reaction for the conversion of dopa into dopaquinone by virtue of its oxidase activity. This tyrosinase acts only when it is in the mature state, under the action of certain biological factors.

A substance is recognized as being depigmenting if it acts directly on the vitality of the epidermal melanocytes in which melanogenesis takes place and/or if it interferes with one of the steps in the biosynthesis of melanin either by inhibiting one of the enzymes involved in melanogenesis or by becoming intercalated as a structural analogue of one of the chemical compounds in the melanin synthesis chain, whereby this chain may then be blocked and thus ensure depigmentation.

The substances most commonly used as depigmenting agents are, more particularly, hydroquinone and its derivatives, in particular its ethers such as hydroquinone monomethyl ether and monoethyl ether. Although they have a certain level of efficacy, these compounds are unfortunately not free of side effects on account of their toxicity, which can make them difficult or even hazardous to use. This toxicity arises from the fact that they interfere with fundamental mechanisms of melanogenesis, by killing cells which then risk disrupting their biological environment and which consequently force the skin to eliminate them by producing toxins.

Thus, hydroquinone is a compound which is particularly irritant and cytotoxic to melanocytes, and whose total or partial replacement has been envisaged by many authors.

Substances have thus been sought which are not involved in the mechanism of melanogenesis, but which act upstream on tyrosinase by preventing its activation, and are consequently much less toxic. Kojic acid is commonly used as a tyrosinase-activation inhibitor, this acid complexing the copper present in the active site of this enzyme. Unfortunately, this compound can give rise to allergic reactions ("Contact allergy to kojic acid in skin care products", Nakagawa M. et al., in Contact Dermatitis, Jan. 95, Vol. 42 (1), pp. 9–13). In addition, this compound is unstable in solution, which somewhat complicates the manufacture of the composition.

It is most particularly sought to use harmless topical depigmenting substances which have good efficacy, with a view to treating regional hyperpigmentations caused by melanocyte hyperactivity, such as idiopathic melasmas, occurring during pregnancy ("pregnancy mask" or chloasma) or during oestro-progestative contraception, localized hyper-pigmentations caused by hyperactivity and proliferation of benign melanocytes, such as senile pigmentation marks known as actinic lentigo, accidental hyperpigmentations or depigmentations, possibly due to photosensitization or to post-lesional cicatrization, as well as certain leukodermias, such as vitiligo. For the latter, (in which the cicatrizations can result in a scar which gives the skin a whiter appearance and leukodermias), failing being able to repigment the damaged skin, the regions of residual normal skin are depigmented in order to give the skin as a whole a uniform white complexion.

Thus, there is a need for a novel agent for bleaching human skin, body hairs and/or head hair which acts as effectively as the known agents, but which does not have their drawbacks, i.e. which is non-irritant, non-toxic and/or non-allergenic to the skin and which is stable in a composition.

The Applicant has found, unexpectedly, that certain aminophenol amide derivatives have depigmenting activity, even at low concentrations, without showing any cytotoxicity.

Aminophenol amide compounds are already known, in particular in compositions intended for bleaching the skin. Mention may be made in particular of documents JP-07061905 and JP-07233022. It is also known, in particular from the document J. Biol. Chem. (1979), 254(23), 12185–91, that N-(4-hydroxyphenyl)-L-glutamine interacts with tyrosinase.

However, these compounds would be difficult to obtain on an industrial scale. They differ in their structure from the compounds which are the subject of the present invention. In addition, neither of these documents discloses or suggests the noteworthy efficacy of the compounds used according to the present invention.

A subject of the present invention is thus the use of certain aminophenol amide derivatives of iformula (I) in and/or for the manufacture of a cosmetic and/or dermatological composition for depigmenting and/or bleaching human skin and/or for removing pigmentation marks from the skin and/or for depigmenting body hairs and/or head hair.

These aminophenol amide derivatives correspond to formula (I) below:

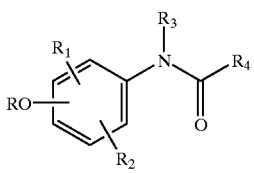

(I)

in which:
R represents
a hydrogen atom;
a linear, branched or cyclic, saturated or unsaturated $C_1$–$C_{24}$ alkyl group optionally hydroxylated with one or more hydroxyl functions;
an aryl group, which may or may not be substituted with one or more functions chosen from: —OH; $NH_2$; —COOH; —$NO_2$; —$OR_5$ with $R_5$=$C_1$–$C_{24}$ alkyl; —$COOR_6$ with $R_6$=$C_1$–$C_{24}$ alkyl; —$NR_7R_8$ with $R_7$=H or $C_1$–$C_{24}$ alkyl, $R_8$=H or $C_1$–$C_{24}$ alkyl;
a group —$COR_9$, $R_9$ representing a linear, branched or cyclic, saturated or unsaturated $C_1$–$C_{24}$ alkyl group optionally hydroxylated with one or more hydroxyl functions, an aryl group which may or may not be substituted with one or more functions chosen from —OH, —$NH_2$, —COOH, —$NO_2$, —$OR_5$, —$COOR_6$, —$NR_7R_8$ in which $R_5$, $R_6$, $R_7$ and $R_8$ have the same definition as above;
$R_1$ and $R_2$, which may be identical or different, represent a group chosen from:
a hydrogen atom;
a linear, branched or cyclic, saturated or unsaturated $C_1$–$C_{24}$ alkyl group optionally hydroxylated with one or more hydroxyl functions;
an aryl group which may or may not be substituted with one or more functions chosen from —OH, —$NH_2$, —COOH, —$NO_2$, —$OR_5$, —$COOR_6$, —$NR_7R_8$, in which $R_5$, $R_6$, $R_7$ and $R_8$ have the same definition as above;
a group chosen from: —OH; —$OQ_1$; —$COQ_2$; —$COOQ_3$; —$NQ_4Q_5$; —$CONQ_6Q_7$; —$SQ_8$; —$CH_2OQ_9$; $Q_1$, $Q_2$, $Q_3$, $Q_4$, $Q_5$, $Q_6$, $Q_7$, $Q_8$ and $Q_9$ being chosen from a hydrogen atom; linear, branched or cyclic, saturated or unsaturated $C_1$–$C_{24}$ alkyl groups optionally substituted with one or more hydroxyl groups; aryls which may or may not be substituted with one or more functions chosen from: —OH, —$NH_2$, —COOH, —$NO_2$, —$OR_5$, —$COOR_6$, —$NR_7R_8$, in which $R_5$, $R_6$, $R_7$ and $R_8$ have the same definition as above; amino acid residues and cyclic or non-cyclic carbohydrate residues;
$R_3$ and $R_4$, which may be identical or different, represent a radical chosen from: a hydrogen atom; linear or branched, saturated or unsaturated $C_1$–$C_{24}$ alkyl groups optionally substituted with one or more hydroxyl groups; cyclic, saturated or unsaturated $C_1$–$C_{24}$ alkyl groups; aryls which may or may not be substituted with one or more functions chosen from: —OH, —$NH_2$, —COOH, —$NO_2$, —$OR_5$, —$COOR_6$, —$NR_7R_8$, in which $R_5$, $R_6$, $R_7$ and $R_8$ have the same definition as above; with the exception of the compound corresponding to the formula (I) for which R=$R_1$=$R_2$=$R_3$=H, $R_4$=$CH_3$, the OH group being placed in the para position relative to the amide.

These compounds are thus already described, in particular, in the documents cited above. They have the advantage of being easy to obtain from simple precursors, such as aminophenols:

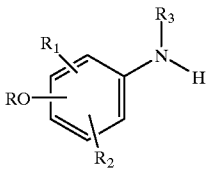

and acids:

$R_4$COOH in which R, $R_1$, $R_2$, $R_3$ and $R_4$ have the same meaning as above, or activated derivatives of these acids. Such reactions are well known to those skilled in the art. Reference may be made, for example, to "Advanced Organic Chemistry, Jerry March, 3rd edition, 1985, pp. 370–377".

According to the present invention, among the linear or branched alkyl radicals having from 1 to 24 carbon atoms, mention may be made advantageously of methyl, ethyl, propyl, isopropyl, butyl, tert-butyl, hexyl, octyl, nonyl, 2-ethylhexyl and dodecyl radicals. Preferably, these radicals have from 1 to 12 carbon atoms. Even more preferably, the alkyl radical generally comprises from 1 to 6 carbon atoms. As lower alkyl radicals, mention may be made of methyl, ethyl, propyl, isopropyl, tert-butyl and hexyl radicals.

Among the linear alkyl radicals having from 1 to 24 carbon atoms, mention may be made in particular of methyl, ethyl, propyl, 2-ethylhexyl, octyl, dodecyl, hexadecyl and octadecyl radicals.

Among the branched alkyl radicals having from 1 to 24 carbon atoms, mention may be made in particular of 2-methylbutyl, 2-methylpentyl, 1-methylhexyl and 3-methylheptyl radicals.

When it is unsaturated, the radical preferably has one or more ethylenic unsaturations, more particularly such as an allyl radical.

When the alkyl radical is cyclic, mention may be made in particular of the cyclohexyl, cholesteryl or tert-butylcyclohexyl radical.

When it is hydroxylated, the radical preferably comprises 1 to 6 carbon atoms and 1 to 5 hydroxyl groups.

Among the monohydroxyalkyl radicals, the preferred radical preferably contains 1 or 3 carbon atoms, in particular the hydroxymethyl, 2-hydroxyethyl or 2- or 3-hydroxypropyl radicals.

Among the polyhydroxyalkyl radicals, the radical preferably has from 3 to 6 carbon atoms and from 2 to 5 hydroxyl groups, such as the 2,3-dihydroxypropyl, 2,3,4-trihydroxybutyl or 2,3,4,5-tetrahydroxypentyl radicals or the pentaerythritol residue.

The alkoxylated radicals are alkyl radicals, in particular such as those described above, preceded by an oxygen atom.

Among the aryl radicals, a phenyl, thiophene or pyridine radical, optionally substituted with at least one halogen atom, a hydroxyl radical, an alkyl radical, a nitro function, a methoxy group or an optionally substituted amine function is preferred. An optionally substituted phenyl radical is preferred.

The term carbohydrate residue is understood to refer to a residue derived in particular from glucose, galactose or mannose, or alternatively from glucuronic acid.

The term amino acid residue is understood to refer in particular to a residue derived from one of the amino acids, such as lysine, glycine or aspartic acid, and the term peptide residue is understood to refer more particularly to a dipeptide or tripeptide residue resulting from the combination of amino acids.

Preferably, the aminophenol amide derivatives used in the present invention are those for which at least one, and preferably all, of the conditions below are satisfied:

R=H or R represents a group —$COR_9$, the group OR is in an ortho or para position relative to the amide, $R_3$=H.

The subject of the present invention is also the use of these aminophenol amide derivatives in and/or for the manufacture of a cosmetic and/or dermatological composition, as tyrosinase inhibitors and/or as melanin synthesis inhibitors.

The subject of the present invention is also the use of these aminophenol amide derivatives in a cosmetic composition for depigmenting and/or bleaching human skin, body hairs or head hair.

The subject of the present invention is also a cosmetic or dermatological, depigmenting or bleaching composition, characterized in that it contains, in a cosmetically and/or dermatologically acceptable medium, at least one aminophenol amide derivative of formula (I) as described above. This composition is more particularly intended for topical use on the skin and/or its superficial body growths (head hair, body hairs and nails).

The present invention also relates to a cosmetic and/or dermatological process for depigmenting and/or bleaching human skin, body hairs or head hair, which consists in applying a composition according to the invention to the skin, body hairs or head hair.

The composition according to the invention is suitable for topical use and thus contains a cosmetically or dermatologically acceptable medium, i.e. one which is compatible with the skin, body hairs or head hair.

The aminophenol amide derivatives of formula (I) can be present in particular in the composition in an amount ranging from 0.01 to 10% and preferably from 0.05 to 5% of the total weight of the composition.

The composition of the invention may be in any pharmaceutical form normally used for topical application, in particular in the form of an aqueous, aqueous-alcoholic or oily solution, an oil-in-water or water-in-oil or multiple emulsion, an aqueous or oily gel, a liquid, pasty or solid anhydrous product, a dispersion of oil in an aqueous phase with the aid of spherules, these spherules possibly being polymeric nanoparticles such as nanospheres and nanocapsules or better still lipid vesicles of ionic and/or non-ionic type.

This composition may be relatively fluid and have the appearance of a white or coloured cream, an ointment, a milk, a lotion, a serum, a paste or a foam. It may optionally be applied to the skin or to the hair in aerosol form. It may also be in solid form and, for example, in the form of a stick. It can be used as a care product and/or as a make-up product. It can also be in the form of a shampoo or a conditioner.

In a known manner, the composition of the invention can also contain the usual adjuvants in the cosmetics and dermatological fields, such as hydrophilic or lipophilic gelling agents, hydrophilic or lipophilic active agents, preserving agents, antioxidants, solvents, fragrances, fillers, screening agents, pigments, odour absorbers and dyestuffs. The amounts of these various adjuvants are those conventionally used in the fields considered, and, for example, from 0.01 to 20% of the total weight of the composition. Depending on their nature, these adjuvants can be introduced into the fatty phase, into the aqueous phase, into lipid vesicles and/or into nanoparticles.

When the composition of the invention is an emulsion, the proportion of the fatty phase can range from 5 to 80% by weight, and preferably from 5 to 50% by weight, relative to the total weight of the composition. The oils, the emulsifiers and the co-emulsifiers used in the composition in emulsion form are chosen from those conventionally used in the field considered. The emulsifier and the co-emulsifier are present in the composition in a proportion ranging from 0.3 to 30% by weight, and preferably from 0.5 to 20% by weight, relative to the total weight of the composition.

As oils which can be used in the invention, mention may be made of mineral oils (liquid petroleum jelly), oils of plant origin (avocado oil, soybean oil), oils of animal origin (lanolin), synthetic oils (perhydrosqualene), silicone oils (cyclomethicone) and fluoro oils (perfluoropolyethers). Fatty alcohols (cetyl alcohol), fatty acids and waxes (carnauba wax, ozokerite) can also be used as fatty substances.

As emulsifiers and co-emulsifiers which can be used in the invention, mention may be made, for example, of fatty acid esters of polyethylene glycol, such as PEG-20 stearate, and fatty acid esters of glycerol, such as glyceryl stearate.

As hydrophilic gelling agents, mention may be made in particular of carboxyvinyl polymers (carbomer), acrylic copolymers such as acrylate/alkylacrylate copolymers, polyacrylamides, polysaccharides, natural gums and clays, and, as lipophilic gelling agents, mention may be made of modified clays such as bentones, metal salts of fatty acids, hydrophobic silica and polyethylenes.

Polyols (glycerol, propylene glycol), vitamins, keratolytic agents and/or desquamating agents (salicylic acid and its derivatives, α-hydroxy acids, ascorbic acid and its derivatives), anti-inflammatory agents, calmants and mixtures thereof can be used in particular as active agents. The aminophenol amide derivatives can also be combined with other depigmenting agents, such as kojic acid or hydroquinone and its derivatives, which allows these derivatives to be used ats doses that are less toxic to the skin. In the event of incompatibility, these active agents and/or the aminophenol amide derivatives can be incorporated into spherules, in particular ionic or non-ionic vesicles and/or nanoparticles (nanocapsules and/or nanospheres), so as to isolate them from each other in the composition.

The invention will now be illustrated with the aid of the examples which follow. The concentrations are given as percentages by weight.

EXAMPLE OF COMPOUNDS

Lauroyl [4-(N-acetylamino)]phenol

An equivalent amount in moles of para-acetylaminophenol and lauroyl chloride are placed in contact at 0° C. in DMF (dilution=15%) in the presence of one molar equivalent of triethylamine. The mixture is allowed to warm to room temperature with stirring and the reaction medium is then poured into water and the product precipitates. It is washed with heptane and then dried under vacuum. The yield is 12%. The elemental analysis is in accordance with the structure.

Tests

A biological test demonstrated the depigmenting activity of the aminophenol amide derivatives of formula (I).

This test corresponds to the one described in patent FR 2,734,825 filed by the Applicant, as well as in the article by R. Schmidt, P. Krien and M. Régnier, Anal. Biochem., 235 (2), 113–18, (1996). This test is thus carried out on a co-culture of keratinocytes and melanocytes.

For each test compound, the $IC_{50}$ value, which corresponds to the micromolar concentration ($\mu$M) for which a 50% inhibition of melanogenesis is observed, is determined.

Moreover, a class is given to each of these compounds as regards their maximum depigmenting activity:

class 1: 10 to 30% inhibition of melanogenesis relative to the control (same experiment without test compound);

class 2: 30 to 60% inhibition of melanogenesis relative to the control (same experiment without test compound);

class 3: 60 to 100% inhibition of melanogenesis relative to the control (same experiment without test compound).

The results are collated in Table (I) below.

|  | $IC_{50}$ ($\mu$M) | Class |
| --- | --- | --- |
| Lauroyl [4-(N-acetylamino)] phenol | >100 | 2 to 100 $\mu$M |
| Kojic acid | 500 | 2 to 500 $\mu$M |

These compounds of formula (I) thus have greater depigmenting efficacy than kojic acid. In addition, they have the advantage of showing no cytotoxicity towards keratinocytes and melanocytes, which is a major defect of the existing depigmenting agents.

EXAMPLES OF COMPOSITIONS

Example 1

Treating Cream

| Cetyl alcohol | 1.05% |
| --- | --- |
| PEG-20 stearate (Myrj 49 sold by the company ICI) | 2% |
| Cyclomethicone | 6% |
| Lauroyl [4-(N-acetylamino)]phenol | 0.5% |
| Carbomer | 0.6% |
| Glycerol | 3% |
| Triethanolamine | 1% |
| Preserving agents | 0.5% |
| Demineralized water | qs 100% |

When applied daily, the cream obtained allows the skin to be bleached.

Example 2

Treating Gel

| Propylene glycol | 10% |
| --- | --- |
| Ethyl alcohol | 40% |
| Glycerol | 3% |
| Lauroyl [4-(N-acetylamino)]phenol | 0.5% |
| Preserving agents | 0.15% |
| Fragrance | 0.15% |
| Demineralized water | qs 100% |

The gel obtained can be used daily and is capable of depigmenting the skin.

Example 3

Treating Stick

| Carnauba wax | 5% |
| --- | --- |
| Ozokerite | 7% |
| Lanolin | 6% |
| Titanium dioxide (pigments) | 20% |
| Rice starch (filler) | 7% |
| EDTA | 0.1% |
| Lauroyl [4-(N-acetylamino)]phenol | 2% |
| Perhydrosqualene | qs 100% |

When used on pigmentation marks, the stick obtained allows these marks to be attenuated, or even makes them disappear altogether.

What is claimed is:

1. A depigmenting or bleaching composition, comprising, in a cosmetically and/or dermatologically acceptable medium, at least one aminophenol amide derivative represented by formula (I):

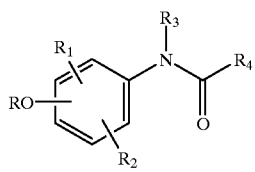

(I)

in which:

R represents a hydrogen atom;

a linear, branched or cyclic, saturated or unsaturated $C_1$–$C_{24}$ alkyl group optionally hydroxylated with one or more hydroxyl functions;

an aryl group, which may or may not be substituted with one or more functions selected from the group consisting of: —OH; —NH$_2$; —COOH; —NO$_2$; and —OR$_5$ wherein R$_5$=$C_1$–$C_{24}$ alkyl; —COOR$_6$ wherein R$_6$=$C_1$–$C_{24}$ alkyl; —NR$_7$R$_8$, wherein R$_7$=H or $C_1$–$C_{24}$ alkyl, R$_8$=H or $C_1$–$C_{24}$ alkyl;

a group —COR$_9$, wherein R$_9$ represents a linear, branched or cyclic, saturated or unsaturated $C_1$–$C_{24}$ alkyl group optionally hydroxylated with one or more hydroxyl functions, an aryl group which may or may not be substituted with one or more functions selected from the group consisting of —OH, —NH$_2$, —COOH, —NO$_2$, —OR$_5$, —COOR$_6$, —NR$_7$R$_8$, wherein R$_5$, R$_6$, R$_7$ and R$_8$ are as defined above;

R$_1$, and R$_2$, which may be identical or different, represent a group selected from the group consisting of:

a hydrogen atom;

a linear, branched or cyclic, saturated or unsaturated $C_1$–$C_{24}$ alkyl group optionally hydroxylated with one or more hydroxyl functions;

an aryl group which may or may not be substituted with one or more functions selected from the group consisting of —OH, —NH$_2$, —COOH, —NO$_2$, —OR$_5$, —COOR$_6$, —NR$_7$R$_8$, wherein R$_5$, R$_6$, R$_7$ and R$_8$ are as defined above; and a group selected from the group consisting of: —OH; —OQ$_1$; —COQ$_2$; —COOQ$_3$; —NQ$_4$Q$_5$; —CONQ$_6$Q$_7$; —SQ$_8$; —CH$_2$OQ$_9$; wherein Q$_1$, Q$_2$, Q$_3$, Q$_4$, Q$_5$, Q$_6$, Q$_7$, Q$_8$ and Q$_9$ are a member selected from the group consisting of a hydrogen atom; linear, branched or cyclic, saturated or unsaturated $C_1$–$C_{24}$ alkyl groups optionally substituted with one or more hydroxyl groups; aryls which may or may not be substituted with one or more functions selected from the group consisting of: —OH, —$NH_2$, —COOH, —$NO_2$, —$OR_5$, —$COOR_6$, and —$NR_7R_8$, wherein $R_5$, $R_6$, $R_7$ and $R_8$ are as defined above; amino acid residues and cyclic or non-cyclic carbohydrate residues;

$R_3$ and $R_4$, which may be identical or different, represent a radical selected from the group consisting of: a hydrogen atom; linear or branched, saturated or unsaturated $C_1$–$C_{24}$ alkyl groups optionally substituted with one or more hydroxyl groups; cyclic, saturated or unsaturated $C_1$–$C_{24}$ alkyl groups; aryls which may or may not be substituted with one or more functions selected from the group consisting of: —OH, —$NH_2$, —$NO_2$, —$OR_5$, —$COOR_6$, —$NR_7R_8$, wherein $R_5$, $R_6$, $R_7$ and $R_8$ are as defined above; with the exception of the compound corresponding to the formula (I) for which R=$R_1$=$R_2$=$R_3$=H, $R_4$=$CH_3$, the OH group being placed in the para position relative to the amide.

2. The composition of claim 1, wherein at least one of the following is satisfied:

R=H or R represents a group —$COR_9$, the group OR is in an ortho or para position relative to the amide, or $R_3$=H.

3. The composition of claim 1, wherein

R=H or R represents a group —$COR_9$, the group OR is in an ortho or para position relative to the amide, and $R_3$=H.

4. The composition of claim 1, comprising from 0.01 to 10% by weight, based on the total weight of the composition, of the aminophenol amide derivative.

5. The composition of claim 1, comprising from 0.05 to 5% by weight, based on the total weight of the composition, of the aminophenol amide derivative.

6. The composition of claim 1, further comprising at least one active agent selected from the group consisting of keratolytic and/or desquamating agents, anti-inflammatory agents, calmants, other depigmenting agents, and mixtures thereof.

7. A method of making the composition of claim 1, comprising incorporating the aminophenyl derivative represented by formula (I) into a cosmetically and/or dermatologically acceptable medium.

8. A method of bleaching or depigmenting skin and/or hair comprising contacting the skin and/or hair with an effective amount of the composition of claim 1.

9. A method of treating skin and/or superficial body growths, comprising applying the composition of claim 1 to the skin and/or superficial body growths.

* * * * *